(12) United States Patent
Smith et al.

(10) Patent No.: US 6,582,399 B1
(45) Date of Patent: Jun. 24, 2003

(54) SYRINGE WITH DETACHABLE SYRINGE BARREL

(75) Inventors: Mark T. Smith, Ontario (CA); Larry Trafford, Ontario (CA)

(73) Assignee: Computer Controlled Syringe Inc. (CA)

( * ) Notice: Subject to any disclaimer, the term of this patent is extended or adjusted under 35 U.S.C. 154(b) by 0 days.

(21) Appl. No.: 09/674,147

(22) PCT Filed: Apr. 27, 1999

(86) PCT No.: PCT/CA99/00335

§ 371 (c)(1),
(2), (4) Date: Oct. 27, 2000

(87) PCT Pub. No.: WO99/55401

PCT Pub. Date: Nov. 4, 1999

(30) Foreign Application Priority Data

Apr. 27, 1998 (CA) .............................................. 2236049

(51) Int. Cl.⁷ ................................................. A61M 1/00
(52) U.S. Cl. ........................ 604/152; 604/187; 604/228
(58) Field of Search ................................ 604/152, 187, 604/228

(56) References Cited

U.S. PATENT DOCUMENTS

| | | | |
|---|---|---|---|
| 4,869,720 A | 9/1989 | Chernack | ..................... 604/228 |
| 5,007,904 A | 4/1991 | Densmore et al. | ........... 604/228 |
| 5,163,917 A * | 11/1992 | Huefner et al. | .............. 604/198 |
| 5,876,861 A * | 3/1999 | Kondo et al. | ........... 204/192.15 |
| 5,928,202 A * | 7/1999 | Linnebjerg | ................... 604/218 |

FOREIGN PATENT DOCUMENTS

| | | | |
|---|---|---|---|
| GB | 2012590 | 8/1979 | ........... A61M/5/315 |
| GB | 2108852 | 5/1983 | ........... A61M/5/315 |
| WO | WO 9920330 | 4/1999 | ........... A61M/5/315 |

* cited by examiner

*Primary Examiner*—Edward K. Look
*Assistant Examiner*—Dwayne J. White
(74) *Attorney, Agent, or Firm*—Katten Muchin Zavis Rosenman

(57) ABSTRACT

The syringe (10) comprises a detachable syringe barrel (14) connected to a housing (12). The housing contains a drive means connected to a plunger (24). The drive means is for extending and retracting the plunger into and out of the detachable syringe barrel. The detachable syringe barrel comprises a stopper (26) at one end thereof in sealing engagement with the interior of the barrel and for releasable engagement with the end of the plunger distal to the drive means. At least a portion of the stopper is flexible between a first position and a second position. In the first position, the flexible stopper may be disengaged from the plunger upon retraction of the plunger away from the detachable syringe barrel. In the second position, the flexible stopper is maybe engaged with the plunger upon extension of the plunger toward the detachable syringe barrel.

25 Claims, 6 Drawing Sheets

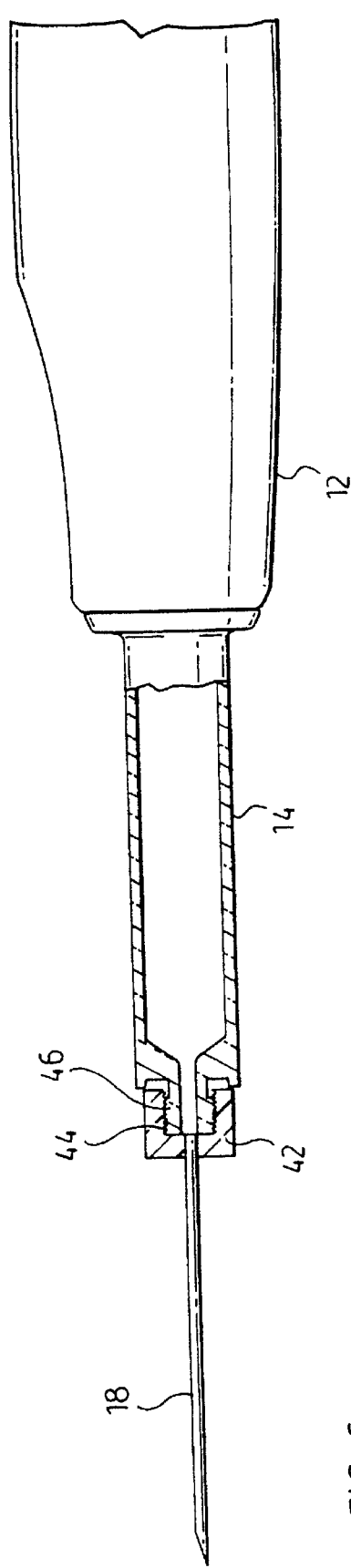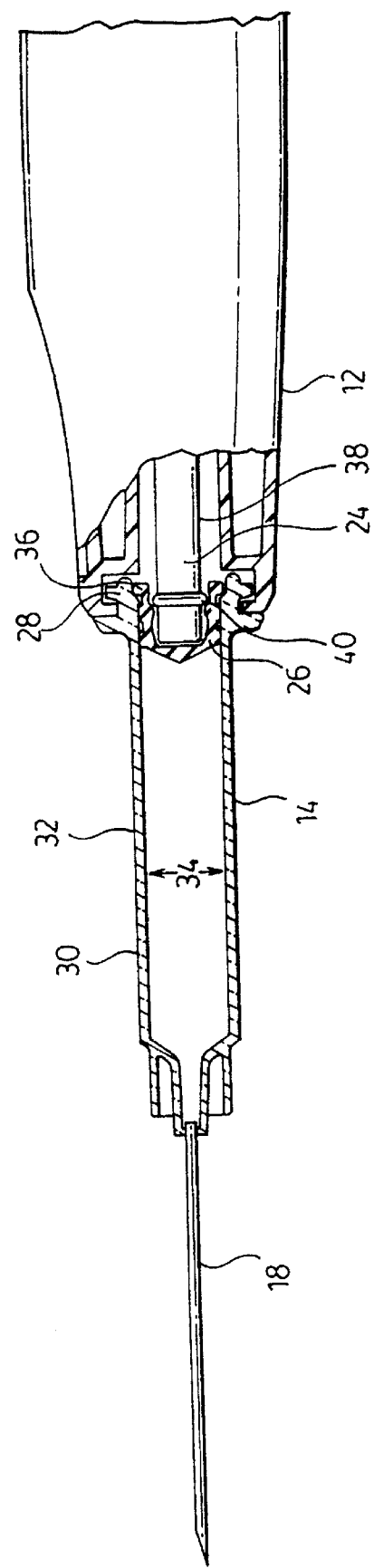
FIG. 6.
FIG. 2.

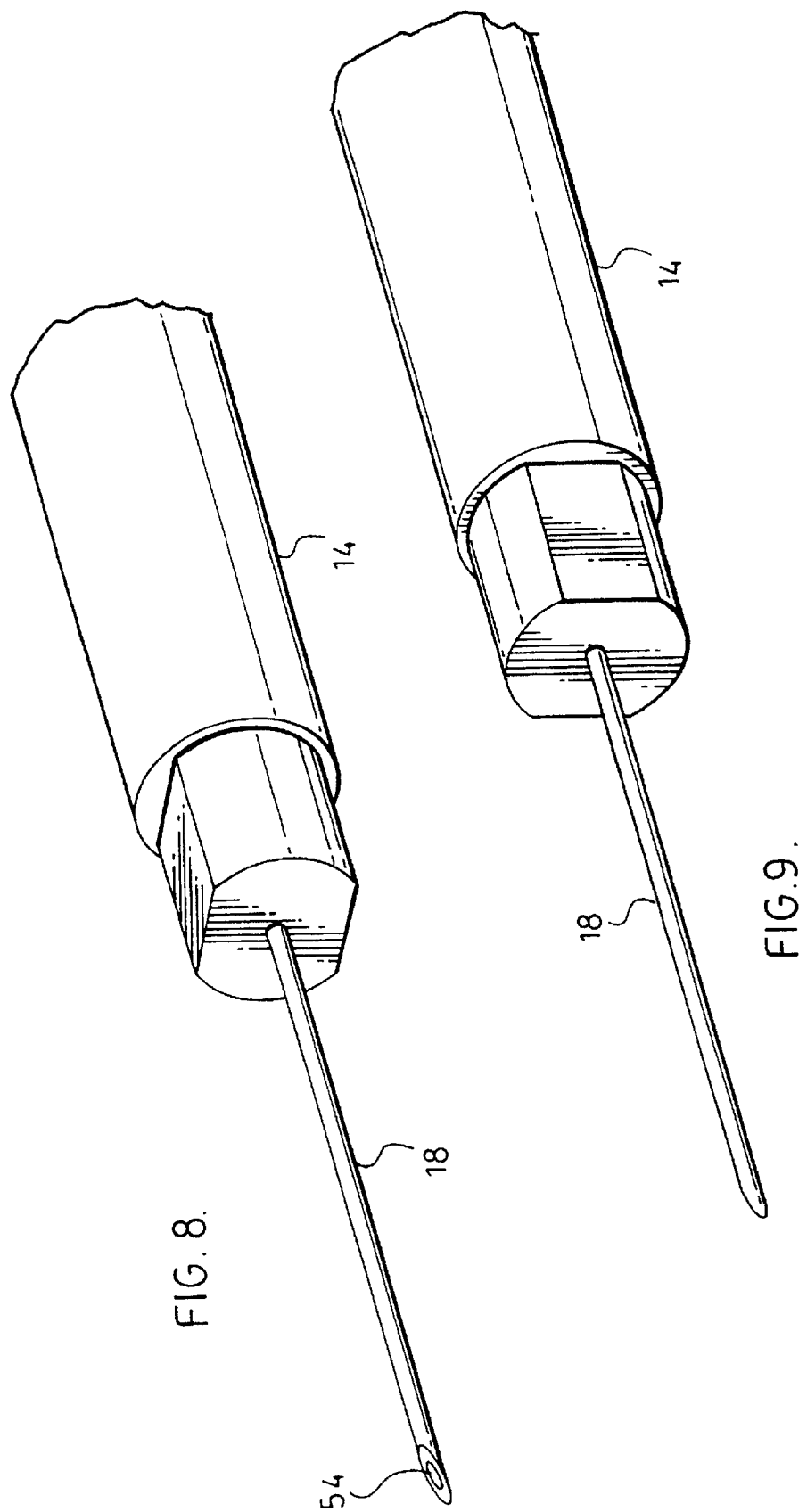

SYRINGE WITH DETACHABLE SYRINGE BARREL

TECHNICAL FIELD

In one of its aspect, the present invention relates to a syringe with a detachable syringe barrel. In another of its aspects, the present invention relates to a detachable syringe barrel for use in a syringe.

BACKGROUND ART

Syringes are will known in the art. Initial syringes were manually operated instruments comprising needles and syringe barrels. After the biocompatible liquid (i.e., drug or other liquid) is dispensed or a sample is taken with these manually operated instruments, the entire instrument including the needle, syringe and plunger is discarded (i.e., the entire instrument is disposable).

Conventional manual syringes, as used in dentistry applications, usually comprise a hollow cylindrical housing having one end adapted to receive a needle and the other end adapted to receive a piston assembly. The outer surface of the housing is provided with a pair of finger grips such that the device can be held firmly between the middle and index fingers of the practitioner's hand. Anaesthetic is commonly supplied in premeasured ampoules which are designed to fit into the housing. The ampoule has one end provided with a pierceable membrane that receives the needle in sealing engagement and another end fitted with a slidable plunger which engages the piston assembly. The piston assembly includes a shaft, one end of which is fitted with a plunger, and an opposing end provided with a thumb rest. In operation, the anaesthetic injection is administered by depressing the plunger with the practitioner's thumb which causes the piston to engage the plunger, thereby forcing anaesthetic from the ampoule via the needle.

There are several disadvantages associated with conventional manual syringes used in dentistry applications. For example, due to uneven thumb pressure applied on the thumb rest, the practitioner has very little control over the flow rate of anaesthetic exiting the needle. As a result it is virtually impossible to achieve a substantially constant flow rate with a manual syringe. Further, many practitioners often complain that, due to the manner by which a conventional manual syringe is grasped, such a syringe offers poor control of the needle tip when administering the injection. As a result, unsteady injections cause unnecessary pain and discomfort to the patient. Still further, it is generally uncontested that the majority of patients dislike the thought of receiving an injection, especially a dental injection. Indeed, this aversion is usually due to the fact that many manual syringes are highly intimidating in appearance.

Thus, a body of prior art developed relating to electronic syringes. For example, U.S. Pat. No. 5,690,618 (Smith et al.), the contents of which are hereby incorporated by reference, describes an electronic syringe which is a pen-style grip electronic syringe which allows a practitioner to administer injections or aspirations at a controlled rate and with a precised degree of hand control. The electronic syringe described in Smith et al. comprises an ampoule receiving first portion wherein an ampoule, premanufactured to contain the biocompatible material of interest, is placed in this first portion of the syringe for administration to the patient. After use, the ampoule is simply discarded.

While the electronic syringe taught by Smith et al. represents a significant advance in the art, there is still room for improvement. Specifically, while electronic syringes have overcome some of the difficulties encountered with manually operated instruments, these electronic syringes are limited to use with a premanufactured ampoule containing the biocompatible liquid of interest. This leads to a number of disadvantages.

First, medical personnel using these electronic syringes do not have the ability to dispense the biocompatible liquid from a bulk storage supply (e.g., a premanufactured bottle of the biocompatible liquid). This leads to a significant cost penalty since the medical personnel must purchase a significant number of premanufactured ampoules to equal the number dosages which could be obtained from bulk storage supply.

Second, the premanufactured ampoules used in conventional syringes are disadvantageous since they must be discarded after use. From an environmental standpoint, this is especially disadvantageous since the ampoules tend to be made of glass, rubber and other unrelated materials.

Third, since there is no standard in electronic syringes and/or the ampoules used therein, a medical practitioner may be in the predicament of having the desired biocompatible liquid available only in an ampoule design which is incompatible with the electronic syringes used by the practitioner.

Accordingly, it would be desirable to provide a syringe device is capable of being used: (i) to withdraw biocompatible liquid from a bulk supply, and (ii) thereafter to administer to a patient a predetermined quantity of the biocompatible liquid. Furthermore, it is desirable to provide a syringe device which has a detachable syringe barrel which can be disposed of or sterilized separately from the device, minimizing the sterilization requirements for the instrument between patients. Still further, it would be desirable to have a syringe barrel capable of simple detachment from the syringe. Still further, it would be desirable if that syringe could be electronically operated.

DISCLOSURE OF THE INVENTION

It is an object of the present invention to provide a syringe which obviates or mitigates at least one of the foregoing disadvantages of the prior art.

Accordingly, in one of its aspects, the present invention provides a syringe comprising:

an outer housing comprising drive means connect to a plunger, the drive means operable to extend and retract the plunger, and a detachable syringe barrel connected to the outer housing, the detachable syringe barrel comprising a stopper at one end thereof in sealing engagement with an interior of the barrel and for releasable engagement with an end of the plunger distal to the drive means, at least a portion of the stopper being flexible between: (i) a first position in which the stopper may be disengaged from the plunger upon retraction of the plunger away from the detachable syringe barrel, and (ii) a second position in which the flexible stopper may be engaged with the plunger upon extension of the plunger toward the detachable syringe barrel.

Thus, the present inventor has developed a novel syringe which obviates or mitigates at least one of the foregoing disadvantages of the prior art. The present syringe comprises a detachable syringe barrel connected to a housing. The housing contains a drive means connected to a plunger. The drive means is for extending and retracting the plunger into and out of the detachable syringe barrel. The detachable syringe barrel comprises a stopper at one end thereof in sealing engagement with the interior of the barrel and for releasable engagement with the end of the plunger distal to the drive means. At least a portion of the stopper is flexible between a first position and a second position. In the first position, the flexible stopper may be disengaged from the plunger upon retraction of the plunger away from the detachable syringe barrel. In the second position, the flexible stopper may be engaged with the plunger upon extension of the plunger toward the detachable syringe barrel. In this manner, the end of the plunger distal to the drive means is releasably engageable with the a portion of the detachable syringe barrel.

In operation, the medical practitioner, actuates the drive means which extends the plunger. As the plunger is extended into the detachable syringe barrel the plunger pushes the flexible stopper from its first position to its second position. In its second position the flexible stopper engages the plunger. The plunger is further extend until the flexible stopper abuts the other end of the detachable syringe barrel. At this point, a needle attached to the detachable syringe barrel is disposed in a bulk supply of biocompatible liquid, the direction of the drive means is reversed and the drive means is actuated thereby retracting the engaged plunger/flexible stopper to fill the detachable syringe to the desired level (i.e., prior to flexible stopper reaching the first position). The syringe may then be used to administer the biocompatible liquid, for example as described in Smith et al. Thereafter, the plunger is retracted to an extent such the stopper adopts the second position thereby allowing the plunger to be disengaged therefrom. The detachable syringe barrel may then be detached from the housing.

In another of its aspects, the present invention provides a syringe barrel for use with a syringe housing, the detachable syringe barrel comprising:

a stopper at one end thereof in sealing engagement with an interior of the barrel and for releasable engagement with an end of a plunger in the syringe housing;

at least a portion of the stopper being flexible between: (i) a first position in which the stopper may be disengaged from the plunger upon retraction of the plunger away from the detachable syringe barrel, and (ii) a second position in which the flexible stopper may be engaged with he plunger upon extension of the plunger toward the detachable syringe barrel.

In one embodiment, the detachable syringe barrel may be adapted to attach to and detach from the syringe housing—this embodiment will be discussed in more detail hereinbelow. In another embodiment, however, it is possible that the syringe barrel may be in the form of an ampoule for use in a device such as the one described in U.S. Pat. No. 5,690,618 (Smith et al.), incorporated by reference hereinabove. In this latter embodiment, the end of the housing opposite the stopper preferably comprises a membrane which may be pierced an end of the needle of the syringe. Thus, for those practitioners who insist on using ampoules, the present syringe barrel may be used advantages to avoid unintentional disassembly of the barrel by removal of the stopper near the plunger.

In a preferred embodiment, the flexible stopper comprises an outwardly projecting rim and when the flexible stopper is in the first position the outwardly projecting rim expands into the internal diameter at the rearward end disengaging the plunger. When the flexible stopper is in the second position, at the frontward end of the detachable syringe barrel, the outwardly projecting rim of the flexible stopper is compressed inwardly engaging the plunger.

In a further aspect of the present invention there is provided a syringe wherein the plunger comprises an outer wall comprising one or more ridges on the outer wall wherein the outward projecting rim is compressed inwardly around the one or more ridges when the flexible stopper engages the plunger in the second position.

In a further aspect of the present invention there is provided a syringe wherein the detachable syringe barrel further comprises a lock attachment for attaching said detachable syringe to said outer housing. In a preferred embodiment, the lock attachment is a twist lock attachment.

In a further aspect of the present invention, there is provided a detachable syringe barrel with a detachable needle. In a preferred embodiment the needle is disposable. In a further preferred embodiment the detachable syringe barrel can be attached to the outer housing of the syringe in a number of different ways to direct the bevel of the needle as desired.

BRIEF DESCRIPTION OF THE DRAWINGS

Embodiments of the present invention will be described with reference to the accompanying drawings, wherein like number designate like parts and in which:

FIG. 2 illustrates a partial longitudinal sectional view a first embodiment of the syringe of the present invention illustrated in FIG. 1;

FIG. 6 illustrates a partial longitudinal sectional view of a second embodiment of the syringe of the present invention;

FIG. 8 illustrates a perspective view of the needle in a first position of the second embodiment of the syringe of the present invention as illustrated in FIG. 2;

FIG. 9 illustrates a perspective view of the needle in a second position of the second embodiment of the syringe of the present invention as illustrated in FIG. 2.

BEST MODE FOR CARRYING OUT THE INVENTION

The present invention will be more particularly described with reference to the preferred embodiments illustrated in the following Figures which depict an electronic syringe particularly adapted for use in dental applications. It is to be understood, however, that the present invention may be embodied in a manual syringe or in a syringe (manual or electronic) adapted for non-dental applications.

Figure 1:
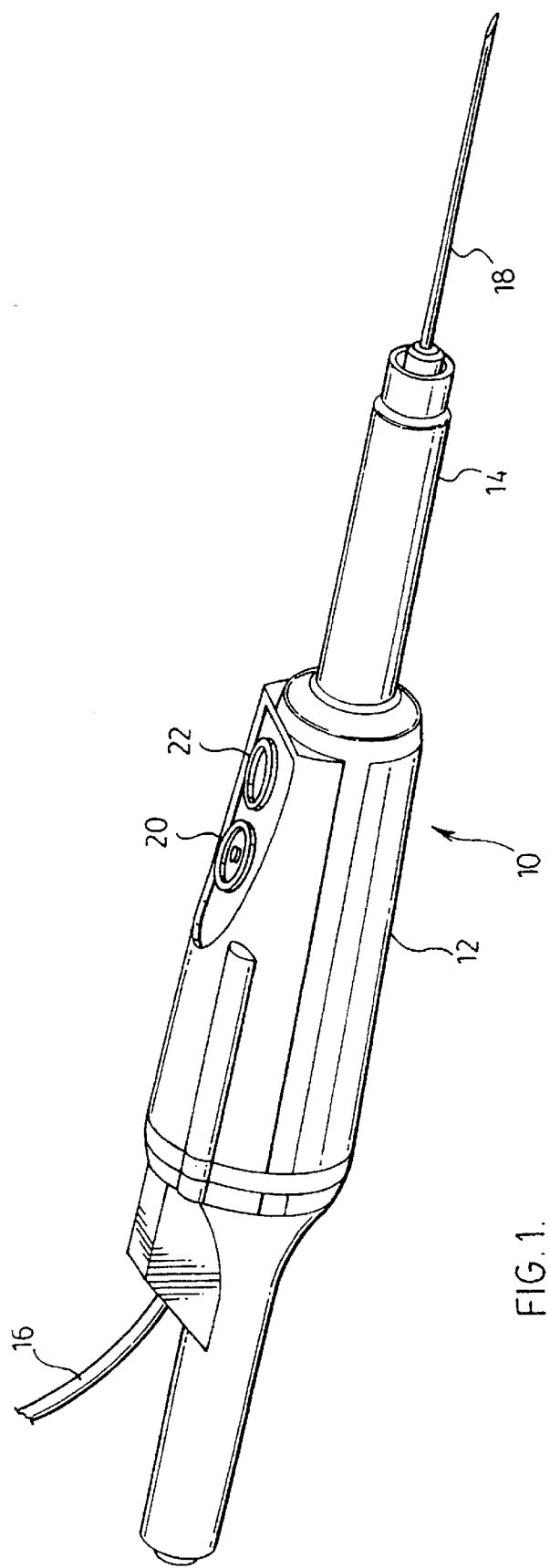
FIG. 1 illustrates a perspective view of a first embodiment of the syringe of the present invention.

Referring to FIG. 1, the syringe 10 comprises an outer housing 12 and a detachable syringe barrel 14. Syringe 10 is an electronic syringe which is attached to a power supply with extension 16. A needle 18 is attached to the detachable syringe barrel 14 and syringe 10 has actuating buttons 20 and 22 for actuating a drive means (not shown) in the outer housing 12 to extend and retract the plunger, respectively.

Referring to FIG. 2, plunger 24 is situated in outer housing 12 and engages the flexible stopper 26 in the detachable syringe barrel 14. The detachable syringe barrel 14 has a rearward end 28, a frontward end 30 and an outer wall 32. The outer wall 32 defines an internal diameter 34 of the detachable syringe barrel 14. The rearward end 28 of the detachable syringe barrel 24 has an internal diameter 34 which is greater than the internal diameter 34 of the frontward end 30 of the detachable syringe barrel 24.

The flexible stopper 26 has an outwardly projecting rim 36. Preferably, the flexible stopper 26 is of a sufficient length so that the flexible stopper 26 is not ripped or twisted when plunger 24 engages said flexible stopper 26. In a preferred embodiment, the flexible stopper 26 is a rubber stopper.

As shown in FIG. 2, plunger 24 has an outer wall 38 with an outer ridge 40 and extends forward and retracts backward when drive means (not shown) in the outer housing 12 are actuated.

Figure 3:
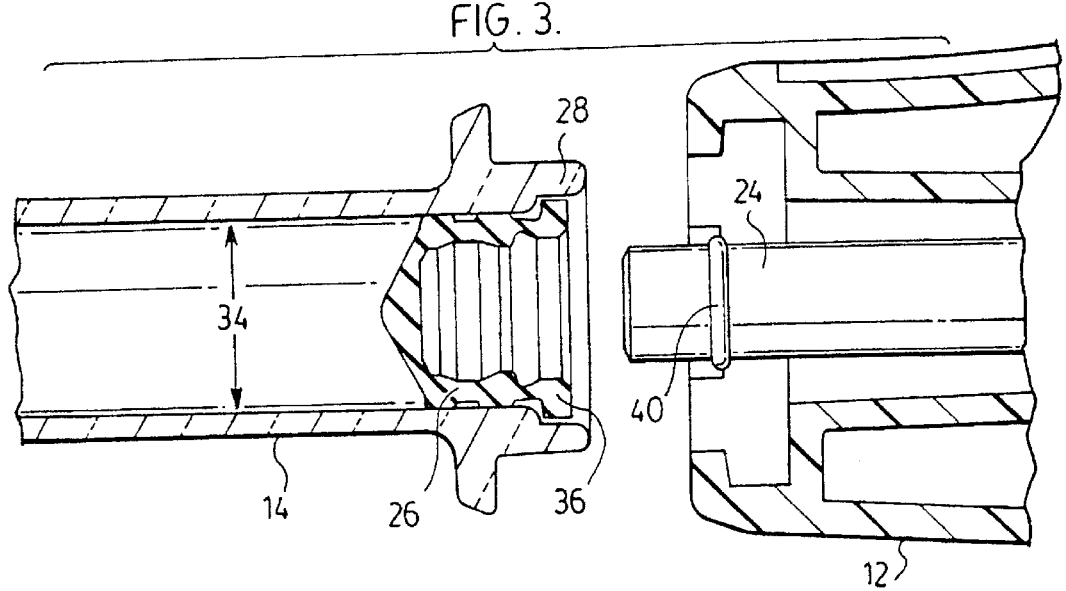
FIG. 3 illustrates a longitudinal sectional view of the flexible stopper in the first position with the disengaged plunger of the syringe of the present invention illustrated in FIG. 1.
Figure 4:
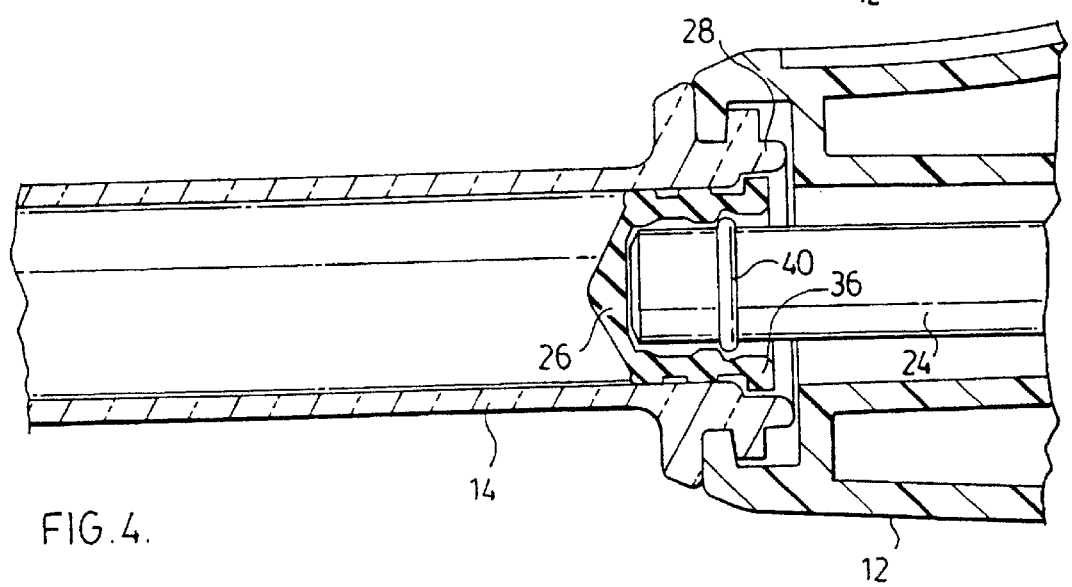
FIG. 4 illustrates a longitudinal sectional view of the flexible stopper and the plunger as the plunger is being extended into the flexible stopper causing the flexible stopper to engage the plunger of the syringe of the present invention illustrated in FIG. 1.
Figure 5:
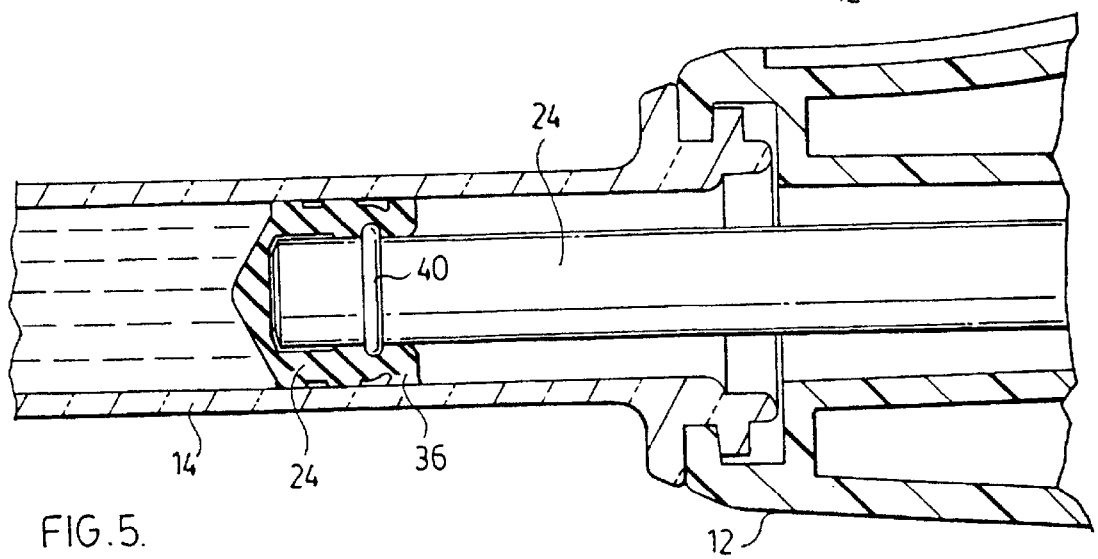
FIG. 5 illustrates a longitudinal sectional view of the flexible stopper in the second position with the engaged plunger of the syringe of the present invention illustrated in FIG. 1.

Referring to FIGS. 3–5, the actuation of plunger 24 in outer housing 12 with the flexible stopper 26 in the detachable syringe barrel 14 is shown. In FIG. 3, the flexible stopper 26 is shown in the first position, disengaged from the plunger 24 and the detachable syringe barrel 14 is detached from the outer housing 12. When the plunger 24 is disengaged from the flexible stopper 26, the outwardly projecting rim 36 expands into the larger diameter 34 of the rearward end 28 of the detachable syringe barrel 14 releasing the outer ridge 40 of the plunger 24 and hence the plunger 24 itself from the flexible stopper 26.

Referring to FIGS. 4 and 5, the second position of the flexible stopper 26 is shown. The detachable syringe barrel 14 is attached to the outer housing 12 and as the plunger 24 is extended into the flexible stopper 26 it pushes the flexible stopper 26 forward causing the outward projecting rim 36 of the flexible stopper 26 to engage the plunger 24 by compressing inwardly against the plunger 24 and around the outwardly projecting rim 36. In this manner the plunger can be extended to the frontward end 30 of the detachable syringe barrel 14. Likewise, the plunger 24 can be retracted together with the engaged flexible stopper to the rearward end 28 of the detachable syringe barrel 14. In this manner, the flexible stopper 26 remains engaged with the plunger 24 while the plunger travels forwards and backwards in the detachable syringe 14. However, the plunger 24 is disengaged from the flexible stopper 26 in the second position to permit the detachable syringe barrel 14 to be detached from the outer housing 12. The detachable syringe barrel 14 can be a disposable barrel or it can be a reusable barrel in which case the barrel will have to be sterilized between uses.

Accordingly, to operate the syringe 10 as shown in FIGS. 4 and 5, the drive means (not shown) in the outer housing 12 is actuated by depressing actuating button 20 causing the plunger 24 to extend forward into the detachable syringe barrel 14 engaging the flexible stopper 14. The plunger 24 is retracted by depressing actuating button 22. At the end of the retraction stroke, the plunger 24 is disengaged from the flexible stopper 26 when the outwardly projecting rim 40 of the flexible stopper 26 expands into the larger internal diameter 34 at the rearward end 28 of the detachable syringe barrel 14. By the extension and retraction of the plunger 24 into the detachable syringe barrel 14, medication can be taken up into the detachable syringe barrel 14 and then administered to the patient.

In a preferred embodiment, there will be a master switch (not shown) which will be placed on the outer housing 12. The master switch will have two settings: a load mode; and a program mode. When the master switch is on the lode mode and the operator pushes the actuating button 20 the plunger 24 will extend into the detachable syringe barrel 14 rapidly engaging the flexible stopper 26 as the plunger 24 extends to the frontward end of the detachable syringe barrel 14. The operator can then push the actuating button 22 and the plunger 24 and flexible stopper 26 will retract sucking the fluid into the syringe. In the program mode, the operator starts to inject the needle and pushes the actuating button 20 extending the plunger into the detachably syringe barrel 14 and engaging the flexible stopper 26 causing the medication or fluid to be expelled initially at a slower pre-set speed so that there is finer control over the amount of medication or fluid initially administered. The operator can press the actuating button 22 to stop the expulsion of medication or fluid at any time. In this manner, this syringe, will be particularly useful in dental applications such as freezing. When the tissues around the teeth are frozen by injection using this syringe, the operator can quickly insert the freezing medication at one site, stop the administration, and move the needle to a different site repeating the cycle until the desired freezing effect is obtained.

In the second embodiment of the syringe shown in FIG. 6, the needle 18 is detachable. At the base of the needle 18 is attached a base portion 42 which has a internally threaded hollow core 44. The detachable syringe barrel 14 has an outer threaded projection 46. The outer threaded projection 46 is in threaded engagement with the internally threaded hollow core 44 thereby attaching the needle 18 to the detachable barrel 14.

Figure 7:
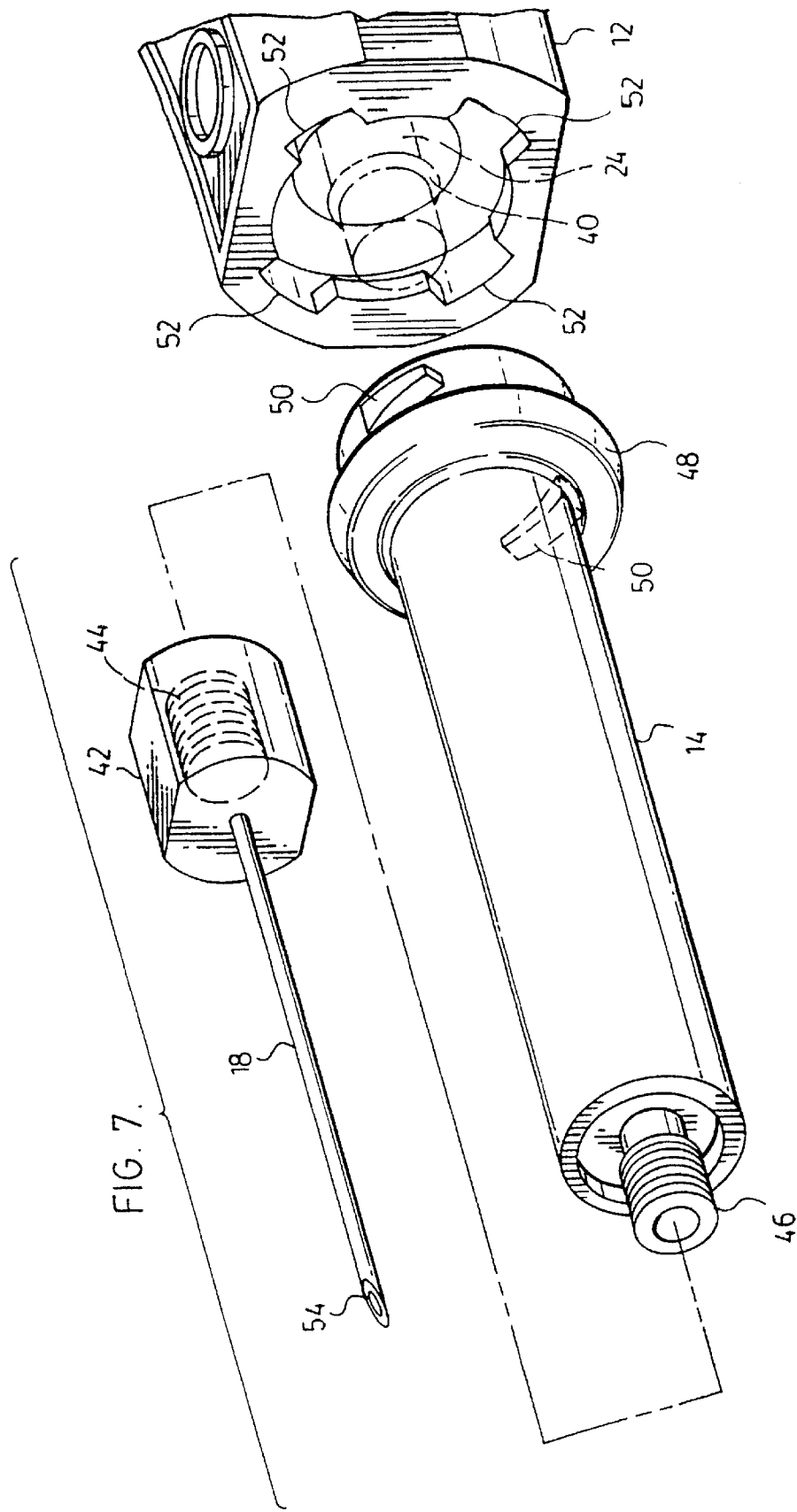
FIG. 7 illustrates an exploded view of the plunger, syringe barrel and detachable needle of the second embodiment of the present invention as illustrated in FIG. 2.

Referring to FIG. 7, there is illustrated the detachable needle 18 and the detachable syringe barrel 14 with a twist lock adjustment 48. The twist lock adjustment 48 has two lugs 50 that are approximately 180 degrees apart from each other on the detachable syringe barrel 14. The outer housing 12 has four openings 52 that arc approximately 90 degrees apart on the outer housing 12. The two lugs 50 can be inserted in any of the two opposing openings 52 and then by twisting the detachable syringe barrel 14 relative to the outer housing 12 the detachable syringe barrel 14 is attached to the outer housing 12. A bevel 54 of needle 18 can be positioned in a desired direction depending on which two openings 52 the operator choses to use to lock the detachable syringe barrel 14 to the outer housing 12, as illustrated in FIGS. 8 and 9. Alternatively, base portion can be designed such that needled 18 may be freely rotated (i.e., through 360°) after attachment to syringe barrel 14.

Figure 10:
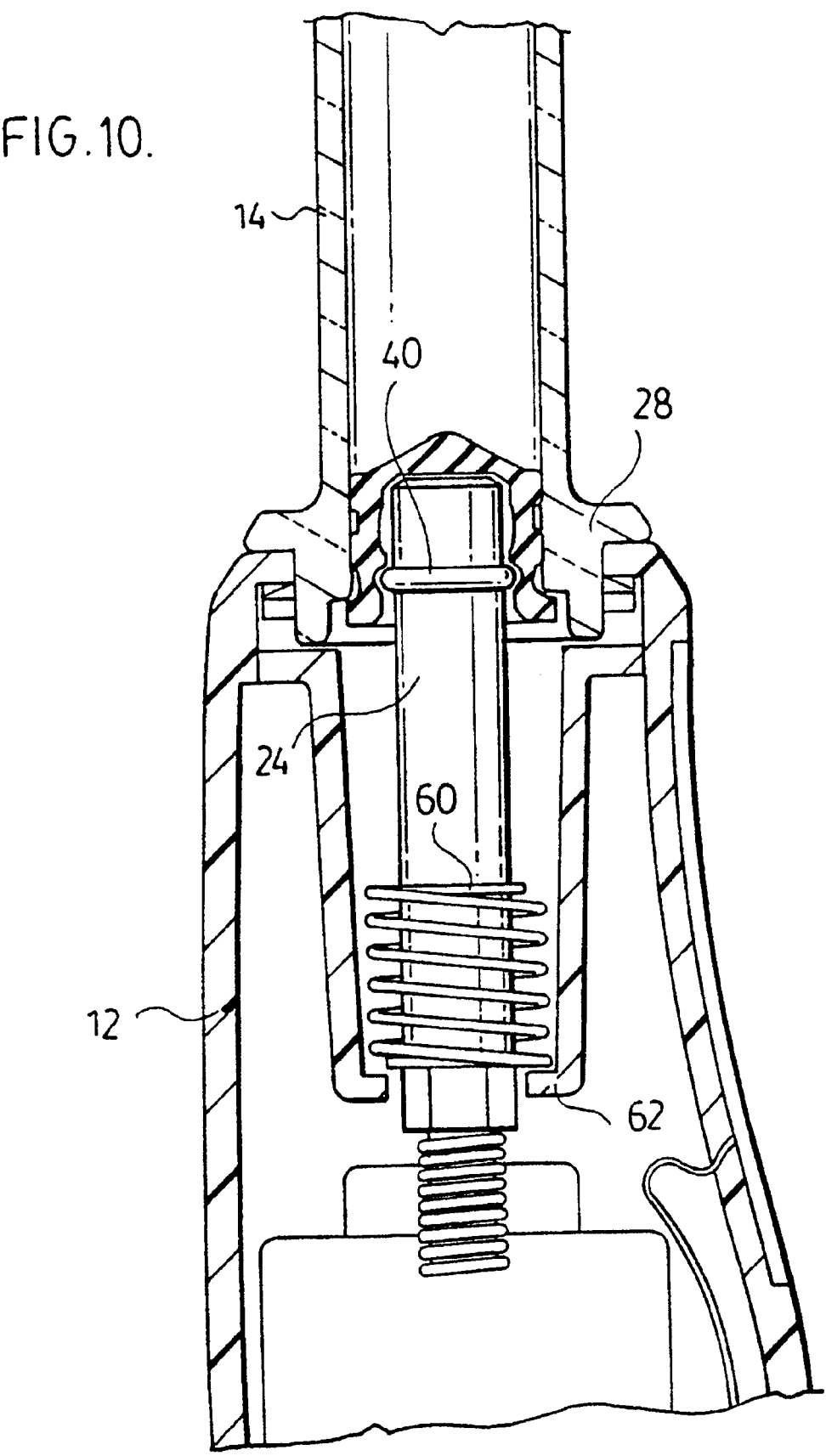
FIG. 10 illustrates a partial longitudinal sectional view of a third embodiment of the syringe of the present invention.

With reference to FIG. 10, there is illustrated an embodiment of how the present syringe barrel may be engaged to housing 12. Specifically, a spring 60 (or other spacer, solid or otherwise—not shown) is disposed at the bottom of a cavity 62 which forms part of housing 12. Thus, spring 60 contracts when plunger 24 is retract into housing 12 and spring 60 expands when plunger 24 is extended into syringe barrel 14. This action of spring 12 serves to compensate for industry variance in carpule length between different manufacturers.

The syringe 10 described above is an electronic syringe. However, it is contemplated that the above described syringe 10 and the detachable syringe barrel 14 could be used with a mechanical, pneumatic or battery charged syringe device. In particular, the drive means in the outer housing 12 for extending and retracting the plunger 24 could be a number of available systems including a motor, pneumatic cylinders, solenoid, electromagnetic or hydraulic systems.

The syringe 10 could be used for administering medications, vitamins, minerals, imaging dyes or the like or for withdrawing fluids from a target organ—i.e., syringe 10 may be used in virtually any application in which a conventional syringe is currently used.

The above description of the preferred embodiments of the present invention are in no way intended to limit the scope of the invention as set out in the appended claims hereto.

What is claimed is:

1. A syringe comprising:

an outer housing comprising drive means connected to a reusable plunger, the drive means operable to extend and retract the plunger, and a detachable syringe barrel connected to the outer housing, the detachable syringe barrel comprising a stopper disposed within the barrel adjacent one end thereof in sealing engagement with an interior of the barrel and for releasable engagement with an end of the plunger distal to the drive means, at least a portion of the stopper being flexible between: (i) a first position in which the stopper may be disengaged from the plunger upon retraction of the plunger away from the detachable syringe barrel, and (ii) a second position in which the flexible stopper may be engaged with the plunger at a point proximal the distal end of the syringe barrel upon extension of the plunger toward the detachable syringe barrel.

2. The syringe defined in claim 1, wherein an end of the detachable syringe barrel proximal the outer housing has a larger internal diameter than an opposite end of the detachable syringe barrel.

3. The syringe defined in claim 2, wherein the stopper in the first position expands into the larger internal diameter.

4. The syringe defined in claim 3, wherein the stopper compressed inwardly engaging the plunger at points along the detachable syringe barrel distal to the larger internal diameter.

5. The syringe defined in claim 4, wherein the stopper comprises an outward projecting rim which expands into the internal diameter at the rearward end disengaging the plunger.

6. The syringe defined in claim 5, wherein the plunger comprises an outer wall comprising one or more ridges on the outer wall wherein the outward projecting rim is compressed inwardly around the one or more ridges when the flexible stopper engages the plunger.

7. The syringe defined in claim 6, wherein the detachable syringe barrel further comprises a lock attachment for attaching the detachable syringe to the outer housing.

8. The syringe defined in claim 7, wherein the lock attachment is a twist lock attachment.

9. The syringe defined in any one of claims 1–8, wherein the detachable syringe barrel is disposable.

10. The syringe defined in any one of claims 1–8, wherein the syringe is an electronic syringe.

11. The syringe defined in any one of claims 1–8, wherein the syringe further comprises a needle which is detachable from the detachable syringe barrel and the needle is disposable.

12. The syringe defined in claim 11, wherein the needle is in threaded engagement with the detachable syringe barrel.

13. A syringe barrel for use with a syringe housing, the syringe barrel comprising:

a stopper disposed within the barrel adjacent one end thereof in sealing engagement with an interior of the barrel and for releasable engagement with an end of a reusable plunger in the syringe housing;

at least a portion of the stopper being flexible between: (i) a first position in which the stopper may be disengaged from the plunger upon retraction of the plunger away from the syringe barrel, and (ii) a second position in which the flexible stopper may be engaged with the plunger at a point proximal the distal end of the syringe barrel upon extension of the plunger toward the syringe barrel.

14. The syringe barrel defined in claim 13, wherein the barrel is detachable from the syringe housing.

15. The syringe barrel defined in claim 14, wherein an end of the syringe barrel proximal the outer housing has a larger internal diameter than an opposite end of the syringe barrel.

16. The syringe barrel defined in claim 15, wherein the stopper in the first position expands into the larger internal diameter.

17. The syringe barrel defined in claim 16, wherein the stopper comprises an outward projecting rim which expands into the internal diameter at the rearward end disengaging a plunger in the syringe housing.

18. The syringe barrel defined in any one of claim 13–17, wherein the syringe barrel is disposable.

19. The syringe barrel defined in any one of claims 13–17, wherein an end of the syringe barrel opposite the stopper comprises a membrane in sealing engagement with the syringe barrel.

20. The syringe barrel defined in any one of claims 13–17, wherein the syringe barrel further comprises a lock attachment for attaching the detachable barrel to the syringe housing.

21. The syringe barrel defined in claim 20, wherein the lock attachment is a twist lock attachment.

22. The syringe barrel defined in any one of claims 13–17, wherein the syringe barrel further comprises a needle which is detachable from the syringe barrel.

23. The syringe barrel defined in claim 22, wherein the needle is in threaded engagement with the detachable syringe barrel.

24. The syringe barrel defined in any one of claims 13–17, wherein the syringe barrel is in the form of an ampoule.

25. The syringe barrel defined in claim 24, wherein the ampoule contains a biocompatible liquid.

* * * * *